United States Patent
Moores et al.

(10) Patent No.: US 10,104,890 B2
(45) Date of Patent: Oct. 23, 2018

(54) COMPOSITIONS AND METHODS FOR CONTROLLING PESTICIDE RESISTANT PESTS

(75) Inventors: Graham David Moores, Hertfordshire (GB); Despina Philippou, Nicosia (CY); Valerio Borzatta, Bologna (IT); Elisa Capparella, Ravenna (IT)

(73) Assignees: Rothamsted Research Limited, Hertfordshire (GB); Endura S.P.A., Bologna (IT)

( * ) Notice: Subject to any disclaimer, the term of this patent is extended or adjusted under 35 U.S.C. 154(b) by 0 days.

(21) Appl. No.: 14/004,506

(22) PCT Filed: Mar. 7, 2012

(86) PCT No.: PCT/GB2012/050500
§ 371 (c)(1),
(2), (4) Date: Dec. 23, 2013

(87) PCT Pub. No.: WO2012/123714
PCT Pub. Date: Sep. 20, 2012

(65) Prior Publication Data
US 2014/0107162 A1 Apr. 17, 2014

(30) Foreign Application Priority Data
Mar. 11, 2011 (GB) .................................. 1104156.3

(51) Int. Cl.
*A01N 43/50* (2006.01)
*A01N 43/30* (2006.01)
*A01N 51/00* (2006.01)

(52) U.S. Cl.
CPC ............. *A01N 43/50* (2013.01); *A01N 43/30* (2013.01); *A01N 51/00* (2013.01)

(58) Field of Classification Search
CPC combination set(s) only.
See application file for complete search history.

(56) References Cited

U.S. PATENT DOCUMENTS

| | | | |
|---|---|---|---|
| 2,878,265 | A | 3/1959 | Forman et al. |
| 2,878,266 | A | 3/1959 | Forman et al. |
| 6,342,613 | B1 | 1/2002 | Borzatta et al. |
| 6,608,232 | B1 | 8/2003 | Jacquot et al. |
| 6,881,869 | B1 | 4/2005 | Jacquot |
| 7,402,709 | B2 | 7/2008 | Borzatta et al. |
| 2005/0255137 | A1* | 11/2005 | Moores ............... A01N 25/00 424/405 |

FOREIGN PATENT DOCUMENTS

| | | |
|---|---|---|
| DE | 101 19 421 A1 | 9/2002 |
| EP | 0617890 A1 | 10/1994 |
| EP | 2289889 A1 | 3/2011 |
| JP | 2006298767 | 11/2006 |
| JP | 2008201710 | 9/2008 |
| WO | 97/19040 A2 | 5/1997 |
| WO | 98/22417 A1 | 5/1998 |
| WO | 03/092378 A1 | 11/2003 |
| WO | 2006/111553 A1 | 10/2006 |
| WO | 2006/111570 A2 | 10/2006 |

OTHER PUBLICATIONS

Garrido-Herrera (hereinafter Herrera) (Controlled Release of Isoproturon, Imidacloprid and Cyromazine from Alginate-Bentonite-Activated Carbon Formulations, J Agric Food Chem, 2006, vol. 54, pp. 10053-10060).*
Bingham, G. et al. Pest Manag Sci. 64(1):81-85 (2008). "Temporal synergism can enhance carbamate and neonicontinoid insecticidal activity against resistant crop pests."
Kang, C.Y. et al. J. Appl. Entomol. 130(6-7):377-385 (2006). "Synergism of enzyme inhibitors and mechanisms of insecticide resistance in Bemisia tabaci (Gennadius) (Horn., Aleyrodidae)."
Ninsin et al., Pest Manag Sci. 61(8):723-727 (2005). "Synergism and stability of acetamiprid resistance in a laboratory colony of Plutella xylostella."
Pap et al., Pest Manag Sci. 57(2):186-190 (2001). "Comparative evaluation of new synergist containing a butynyl-type synergophore group and piperonyl butoxide derivatives."
Roy et al., Journal of Plant Protection Research, 49(2):225-228 (2009). "The synergist action of piperonyl butoxide on toxicity of certain insecticides applied against helopeltis theivora waterhouse (heteroptera miridae) in the dooars tea plantation of North Bengal India."
Puinean et al., "Amplification of a Cytochrome P450 Gene Is Associated with Resistance to Neonicotinoid Insecticides in the Aphid Myzus persicae", PLoS Genet. 6(6):e1000999 (2010).

* cited by examiner

*Primary Examiner* — Kathrien A Cruz
(74) *Attorney, Agent, or Firm* — Nixon Peabody LLP; David S. Resnick; Ravinderjit Braich

(57) ABSTRACT

Provided are compositions comprising (i) a neonicotinoid; and (ii) a compound of formula (I) or (II), preferably wherein the composition is a pesticide composition, for example an insecticide composition. Also provided is use of a compound of formula (I) or (II) as a neonicotinoid synergist and use of a compound of formula (I) or (II) in combination with a neonicotinoid. Further provided are methods for controlling pests.

9 Claims, No Drawings

COMPOSITIONS AND METHODS FOR CONTROLLING PESTICIDE RESISTANT PESTS

CROSS-REFERENCE TO RELATED APPLICATIONS

This application is a 35 U.S.C. § 371 National Phase Entry Application of International Application No. PCT/GB2012/050500 filed Mar. 7, 2012, which designates the U.S., and which claims benefit of Great Britain Application No. 1104156.3, filed Mar. 11, 2011, the contents of each of which are incorporated herein by reference in their entireties.

The present application relates to pesticide synergists, in particular to synergists which improve the effectiveness of neonicotinoids against pests showing resistance thereto.

Insecticide resistance has become progressively more widespread since first being scientifically recorded in 1914. Over 500 insect and mite species now show tolerance to pesticides, and pesticide resistance has become a serious threat to the future success of pest control using chemicals.

Many insects possess detoxification systems, which evolved originally to protect the insect from natural toxins in the environment. Metabolism of the insecticide may occur before it reaches its target-site when it comes into contact with those detoxifying enzymes that render it either less toxic or more easily excreted, or both. This is true for many types of insecticides, including neonicotinoids.

Neonicotinoids are a class of insecticides which act on the central nervous system of insects with lower toxicity to mammals. Neonicotinoids are among the most widely used insecticides worldwide and resistance of insects to neonicotinoids is an increasing problem.

In order to try and prevent or overcome the resistance of pests to pesticides, one strategy is to administer a pesticide synergist at the same time, or shortly before administration of the pesticide. The intention behind this strategy is for the synergist to inhibit the detoxification systems of the pest so that the pesticide is more effective. Whilst this strategy has been employed effectively in some circumstances, there is still a need for improved compositions and methods for improving the effectiveness of pesticides, especially against pesticide resistant insects.

In particular, there is a need for improved methods and compositions for improving the effectiveness of neonicotinoids against neonicotinoid-resistant pests.

SUMMARY OF THE INVENTION

According to one aspect of the present invention, there is provided a composition comprising (i) a neonicotinoid; and (ii) a compound of formula I or II.

Preferably, the composition is a pesticide composition, preferably an insecticide composition.

Preferably, the composition comprises a rapid release formulation of the compound of formula I or II, and a non-rapid release formulation of the neonicotinoid.

According to another aspect of the present invention, there is provided use of a compound of formula I or II as a neonicotinoid synergist.

In this respect, the term "neonicotinoid synergist" means that the compound of formula I or II is capable of making the neonicotinoid effective against neonicotinoid-resistant pests, or is capable of making the neonicotinoid more effective against neonicotinoid-resistant pests and/or neonicotinoid-susceptible pests.

In this respect, the term "neonicotinoid-susceptible pest" means a pest which is susceptible to action of the neonicotinoid. For example, a neonicotinoid-susceptible pest could be a pest which can be disabled or killed by a neonicotinoid.

Advantageously, use of a compound of formula I or II as a neonicotinoid synergist means that less neonicotinoid is needed in order to achieve the same results as use of a neonicotinoid alone in relation to neonicotinoid-susceptible pests.

According to another aspect of the present invention, there is provided use of a compound of formula I or II in combination with a neonicotinoid.

According to another aspect of the present invention, there is provided a method for controlling pests, the method comprising contacting the pests with (i) a compound of formula I or II and (ii) a neonicotinoid.

Preferably, the pests are contacted with a compound of formula I or II before being contacted with the neonicotinoid.

Preferably, the pests are contacted with a compound of formula I or II at least about 30 minutes before being contacted with the neonicotinoid, preferably at least about 1 hour, preferably at least about 2 hours, preferably at least about 3 hours, for example about 4 hours before being contacted with the neonicotinoid.

Preferably, the pests are contacted directly with a compound of formula I or II and a neonicotinoid. For example, the compound of formula I or II and the neonicotinoid may be sprayed directly onto the pests. Alternatively, the pests may be contacted indirectly with a compound of formula I or II and a neonicotinoid. For example, a surface upon which a pest may be found (for example a crop) may be contacted with a compound of formula I or II and the neonicotinoid.

According to another aspect of the present invention, there is provided a method for controlling pests, the method comprising contacting the pests with a composition of the present invention.

Preferably, the pests are contacted directly with a composition of the present invention. For example, a composition of the present invention may be sprayed directly onto the pests. Alternatively, the pests may be contacted indirectly with a composition of the present invention. For example, a surface upon which a pest may be found (for example a crop) may be contacted with a composition of the present invention.

Preferably, the neonicotinoid is selected from imidacloprid, acetamiprid, clothianidin, dinotefuran, nitenpyram, thiacloprid and thiamethoxam.

Most preferably, the neonicotinoid is imidacloprid.

Preferably, the pests are neonicotinoid-resistant pests or neonicotinoid-susceptible pests.

Preferably, the pests are insects.

Preferably, the pests are selected from sucking or chewing insects, for example from Hemiptera, Coleoptera, Diptera and Lepidoptera.

Preferably, the pests are selected from *Helicoverpa armigera, Helicoverpa punctigera, Heliothis virescens, Aphis gossypii, Myzus persicae, Pseudoplusia includens, Wiseana cervinata, Bemisia tabaci, Meligethes aeneus, Leptinotarsa decemlineata, Tuta absoluta Spodoptera* sp. and mosquito species.

Preferably, the pests are aphids, for example apterous aphids.

DETAILED DESCRIPTION OF THE INVENTION

The invention relates to compositions and methods for controlling neonicotinoid-resistant pests. In particular, the invention relates to novel compositions comprising a neonicotinoid and a neonicotinoid synergist.

Detailed examples of the invention are set out below.

Within this specification embodiments have been described in a way which enables a clear and concise specification to be written, but it is intended and will be appreciated that embodiments may be variously combined or separated without parting from the invention.

Within this specification, reference to a compound of formula I means a compound having the following structure:

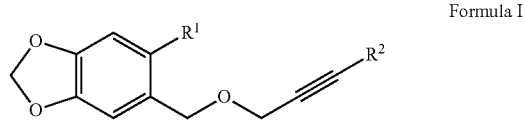

Formula I wherein,
$R^1$ is a $C_1$ to $C_{12}$ alkyl; and
$R^2$ is selected from H and a $C_1$ to $C_5$ alkyl.

Within this specification, reference to a compound of formula II means a compound having the following structure:

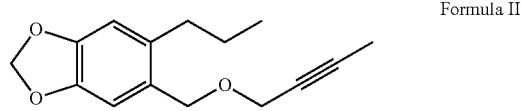 [SMILES: CC#CCOCc1cc2c(cc1CCC)OCO2]

Formula II

Within this specification, the term "EN 126" means a compound of formula II.

Within this specification, the term "neonicotinoid-resistant pest", means a pest, for example an insect, which shows at least some resistance to a neonicotinoid. The resistance may be partial or complete and it will be appreciated that all degrees of resistance are included the meaning of this term, whether they be very low resistance, low resistance, high resistance, very high resistance or total resistance.

The World Health Organisation has defined resistance as "the development of an ability in a strain of insects to tolerate doses of toxicant that would prove lethal to the majority of individuals in a normal population of the same species". Pesticide resistance is therefore to be similarly construed, although the main pests addressed herein are insects.

Within this specification, the terms "comprises" and "comprising" are interpreted to mean "includes, among other things". These terms are not intended to be construed as "consists of only".

Within this specification, the term "about" means plus or minus 20%, more preferably plus or minus 10%, even more preferably plus or minus 5%, most preferably plus or minus 2%.

Within this specification, it will be appreciated that reference to the term "controlling pests" includes reference to killing or disabling pests. Preferably, the term means killing or disabling all or a substantial proportion of a population of pests contacted with a composition of the present invention.

The term "substantial portion" may mean at least about 50%, at least about 60%, at least about 70%, at least about 80%, at least about 90%, at least about 95%, at least about 98%, or at least about 99%.

As described herein, the composition of the invention may comprise a rapid release formulation of the compound of formula I or II, and a non-rapid release formulation of the neonicotinoid. Suitable rapid release and non-rapid release formulations are described in detail in International patent application number PCT/GB03/01861, published as WO 03/092378 on 13 Nov. 2003.

For example, the rapid release formulation and the non-rapid (sustained) release formulation may be comprised in the composition in physical admixture. Alternatively, the rapid release formulation and the non-rapid release formulation may be administered separately, but be brought into contact with the pest at about the same time, avoiding the need to revisit the site of the pest in order to apply the second of the two formulations. Both formulations would thereby come into contact with the pest within the order of seconds, preferably within 10 seconds and more preferably, within one or two seconds, of each other rather than in the order-of minutes or longer. Preferably, the formulations are administered simultaneously.

The rapid release formulation is suitably any standard pesticide formulation known to those skilled in the art or yet to be discovered and suitable for the purpose. Such formulations include, for example, wettable powders, granulates, emulsifiable concentrates and ultra-low volume formulations to which water can be added to form an emulsion, a suspension and the like. Preferably, the rapid release formulation, comprising a compound of formula I or II, is in the form of an emulsifiable concentrate.

The non-rapid release formulation is suitably any non-immediate release formulation known in the art or yet to be discovered, such as sustained, controlled or slow release formulations suitable for the purpose. Preferably, the non-rapid release formulation is one that prevents an effective dose of the pesticide from being released or coming into effective contact with the pest or its target in the pest until the compound of formula I or II has at least begun its effect on its target in the pest.

Suitably, the non-rapid release formulation prevents release of the pesticide or contact thereof with the pest for at least about 30 minutes, preferably at least about 1 hour, preferably at least about 2 hours, preferably at least about 3 hours, for example about 4 hours after application of the composition. Such formulations include, for example, the pesticide encapsulated in a degradable capsule and preferably comprise micro-encapsulation technology.

The non-rapid release formulation preferably comprises an amount equivalent to a standard dosage of the pesticide.

The amount of the compound of formula I or II should be sufficient to prevent or reduce the resistance of the pest(s) to the pesticide and will depend on pest size (eg a white fly needs a lot less than an *H. armigera* grub), degree of resistance etc, but is determinable by those skilled in the art.

The pest(s) against which the composition of the invention is/are directed can be any which are known to offer at least some resistance to a neonicotinoid and which it is considered necessary to disable and/or kill Examples include those that attack or damage or otherwise reduce the commercial or other value of a substrate, such as crops, particularly arable crops, such as food and material crops including cotton.

Other pests include those that are a nuisance to or an adversary of other living organisms, including mammals, such as humans.

In one example, the pest(s) may include one or more of *Helicoverpa armigera, Helicoverpa punctigera, Heliothis virescens, Aphis gossypii, Myzus persicae, Pseudoplusia includens, Wiseana cervinata, Bemisia tabaci, Meligethes*

*aeneus, Leptinotarsa decemlineata, Tuta absoluta Spodoptera* sp. and mosquito species.

For administration to the surface upon which a pest may be found (also termed "substrate"), any method known in the art for application of a pesticide or the like to a substrate may be used and may depend upon factors such as the particular substrate (e.g. crop), target pest stage of the crop and the like.

Examples of such methods include spraying by ground or aerial application. For administration to crops, particularly over vast areas such as the Australian cotton fields, it is preferred to spray a composition comprising a suspension or emulsion of one or both of the formulations in water, optionally also comprising a surfactant or other excipients, or an ultra-low volume (omitting the water) composition, supplied in a tank, such as one adapted to be transported by aircraft or, for example as in the case of whitefly sprays, by ground rig (such as tractor, tank or boom spray).

The rate of administration of the compositions according to the invention will accord with known or approved (registered) rates of the active ingredients of each of the formulations.

Compounds of the present invention may be synthesized according to the methods described below.

Compounds of formula I, in which $R^1$ is a $C_1$ to $C_{12}$ alkyl, and $R^2$ is selected from H and a $C_1$ to $C_5$ alkyl,

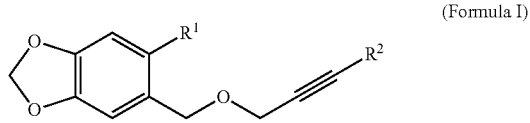

(Formula I)

can be prepared by known chemical reactions such as, for example:

A) Condensation (etherification) of the halogenomethyl derivative of formula III, in which $R_1$ represents a $C_1$-$C_{12}$ alkyl, and Hal is Cl or Br,

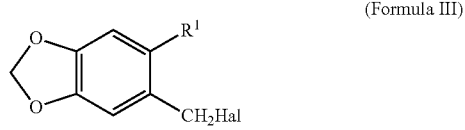

(Formula III)

with the suitable alcohol of a compound of R≡C—$CH_2OH$ (Formula IV), in which $R_2$ represents H or a $C_1$-$C_5$ alkyl, in the presence of a suitable base such as sodium or potassium hydroxide, sodium or potassium carbonate in neat or in an inert aromatic solvent such as toluene or xylene at a temperature between 60° C. and 140° C.; neat or in toluene are preferred.

B) Condensation (etherification) of the halogenomethyl derivative of formula III in which $R_1$ represents a $C_1$-$C_{12}$ alkyl, and Hal is Cl or Br,

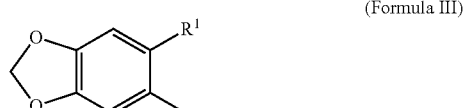

(Formula III)

with the suitable alkaline alcoholate of a compound of $R_2$≡C—$CH_2OMe$ (Formula V) in which $R_2$ represents H or a $C_1$-$C_5$ alkyl and Me is sodium or potassium, in a suitable solvent such as N,N-dimethylformamide, N,N-dimethylacetamide, N-methyl pyrrolidone, tetrahydrofurane, 2-methyltetrahydrofurane or dioxane at a temperature between 50° C. and 150° C. A temperature between 50° C. and 80° C. is preferred.

C) Condensation (etherification) of the hydroxymethyl derivative of formula VI, in which $R_1$ represents a $C_1$-$C_{12}$ alkyl,

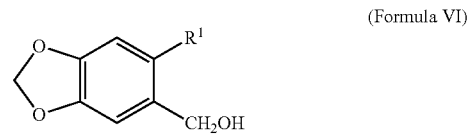

(Formula VI)

with the suitable alkyne halogenide of a compound of $R_2$≡C—$CH_2Hal$ (Formula VII) in which $R_2$ represents H or a $C_1$-$C_5$ alkyl and Hal is Cl, Br or I (preferably Br) in the presence of a suitable base such as sodium hydride and in a suitable solvent such as N,N-dimethylformamide, N,N-dimethylacetamide, N-methylpyrrolidone, tetrahydrofurane, 2-methyltetrahydrofurane or dioxane at a temperature between 50° C. and 150° C. Temperatures between 50° C. and 80° C. are preferred.

D) Condensation (etherification) of the halogenomethyl derivative of formula III, in which $R_1$ represents a $C_1$-$C_{12}$ alkyl and Hal is Cl or Br,

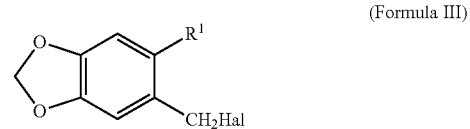

(Formula III)

with the suitable alcohol of a compound of $R_2$≡C—$CH_2OH$ (Formula IV) in which $R_2$ represents H or a $C_1$-$C_5$ alkyl, in the presence of a metal oxide such as zinc oxide and a suitable apolar aprotic solvent such as dichloromethane or dichloroethane and at temperatures between 20° C. and 90° C., as described in U.S. Pat. No. 6,320,085. Temperatures between 20° C. and 40° C. are preferred.

E) Condensation (etherification) of the hydroxymethyl derivative of formula VI, in which $R_1$ represents a $C_1$-$C_{12}$ alkyl,

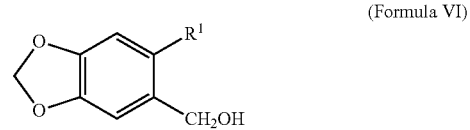

(Formula VI)

with the suitable alcohol of a compound of $R_2$≡C—$CH_2OH$ (Formula IV) in which $R_2$ represents H or a $C_1$-$C_5$ alkyl, in the presence of an efficient amount of a heterogeneous catalyst such as a zeolite in acidic form alone or in combination with a mineral acid as described in U.S. Pat. No. 6,608,232. The reaction is preferably carried out in neat at temperatures between 50° C. and 100° C.

Another possible synthetic pathway is to get compounds of formula I where $R_2$ is hydrogen by the known and shown condensation reactions with an alkylation reagent of a compound of $R_2$—O—$SO_2$—O—$R_2$ (Formula VIII) or $R_2$-Hal (Formula IX), in which $R_2$ represents a $C_1$-$C_5$ alkyl and Hal is Cl, Br or I, in the presence of an anionisation agent such as amide base, a metallic alcoholate or an alkali metal as described in U.S. Pat. No. 6,881,869.

The compounds of formula III can be obtained from compounds of formula X,

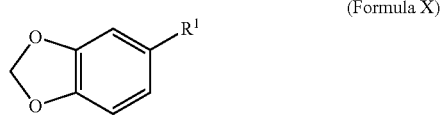

(Formula X)

by the well known reaction of halogenomethylation of a compound of formula X with formaldehyde or paraformaldehyde in the presence of aqueous concentrated hydrochloric acid or hydrobromic acid as described, for example, in U.S. Pat. No. 2,878,265 and U.S. Pat. No. 2,878,266.

The compounds of formula VI can be obtained from the compounds of formula III by reaction with the suitable alkaline acetate and subsequent hydrolysis as described, for example, in U.S. Pat. No. 7,402,709.

The compounds of formula X can be obtained through the well known step of acylation of benzodioxole ring and subsequent reduction as described in U.S. Pat. No. 6,342,613.

Synthesis of 5-(but-2-ynyloxymethyl)-6-propyl-benzo[1,3]dioxole (EN 126)

In a flask equipped with a stirrer, 16 g (0.41 moles) of sodium hydride (60% w/w in mineral oil) and 400 ml of N,N-dimethylformamide are placed. The mixture is cooled to 0° C.-5° C. under stirring and a nitrogen atmosphere. A solution of 75 g (0.38 moles) of 5-(hydroxymethyl)-6-propyl-benzo[1,3]dioxole in 80 ml of N,N-dimethylformamide is then added slowly and stirred for a further hour at room temperature.

The mixture is then cooled to 0° C.-5° C. and 50.5 g (0.38 moles) of 1-bromo-2-butyne are added slowly keeping the temperature at 0° C.-5° C. The reaction is then stirred for a further two hours at room temperature.

The mixture is then cooled to 5° C. and 1000 ml of water is added and extracted with diisopropyl ether (3×200 ml). The organic phases are collected, dried on anhydrous sodium sulfate, filtered and evaporated u.v. (30° C./21 mbar). The oil residue is then distilled at 118° C.-125° C./0.3 mbar obtaining 63.3 g of an oil product (GC title 98.8%) whose NMR and MS analyses correspond to those of the aforementioned compound.

According to one aspect of the present invention, there is provided a method for synthesizing a compound of formula I or II, for example as exemplified herein.

The present invention therefore further provides:

(a) the use of a composition according to the invention in the treatment or prevention of pesticide resistance;

(b) the use of a composition according to the invention in the treatment or prevention of damage to or destruction of a substrate by a pest;

(c) the use of a composition according to the invention in pest control; and (d) a method for preparing a composition according to the invention, which method comprises bringing a compound of formula I or II and a neonicotinoid into physical admixture.

EXAMPLE

Insects

Aphids for bioassays were reared on Chinese cabbage leaves (*Brassica rapa* L. var. Pekinensis c.v Wong Bok) (Brassicaceae) in small plastic box-cages (Blackman boxes) (Stewart Plastics Ltd, Surrey, UK) maintained at 18±2° C. with a 16 h light: 8 h dark photoperiod. Each box contained two adult aphids placed on a leaf and left for 5 days to produce nymphs. After the 5th day the adults were removed and their esterase levels determined to ensure that no contamination or loss of esterase expression (reversion) among the different clones had occurred during the rearing process. After approximately 13-15 days adults were used for bioassays.

Clone 5191A was collected from tobacco in Greece in 2007, and established from a single parthenogenetic female.

Chemicals

Technical PBO ('Ultra', 94%) and PBO analogues (>90%). Technical imidacloprid (analytical standard 99.7%) was obtained from Promochem Ltd, Welwyn Garden City, UK.

Insect Bioassay

Apterous aphids were transferred from Blackman boxes (section 2.1.1) to the abaxial surface of Chinese cabbage leaf discs (approximately 10 adults per leaf disc) held on 1% agar in plastic containers (4 cm in diameter, A.W. Gregory & Co Limited, Kent, UK). The upper edge of each container was coated with Fluon® (Whitford Plastics, Cheshire, UK) to prevent aphid escape from the leaf surface. Netted lids were added to ensure apterous aphids could not escape. After allowing 30 min for the aphids to settle, each was dosed with 0.25 µL of 1 g $L^{-1}$ synergist dissolved in acetone or acetone only using a Burkard microapplicator (Burkhard Scientific, Middx, UK). Synergist concentrations chosen conferred no significant mortality compared to the acetone control treatment in preliminary bioassays. Five hours later, aphids were further treated with 0.25 µL imidacloprid in acetone at a range of concentrations, at least 3 replicates per concentration per bioassay. Controls were treated with 0.25 µL of acetone or 1 g $L^{-1}$ synergist in acetone and after 5 h with a further 0.25 µL of acetone. This 5 h pre-treatment time had been found to be optimal for *M. persicae* and PBO.

Treated aphids were kept at 18±2° C. and 16 h light: 8 h dark photoperiod and scored 72 h after treatment. Aphids incapable of co-ordinated movement (after gentle touching with a paint brush if necessary) were scored as dead. All bioassays were performed a minimum of three times.

Analysis

Pooled raw data from at least three separate bioassays were analysed by probit analysis using the statistical programme PC Polo Plus (LeOra, Software, Berkeley, USA). Polo Plus programme calculated the concentrations required to kill 50% of the population ($LC_{50}$), 95% confidence limits (CL95%), slopes with standard errors (SE), chi-square ($\chi2$) and degrees of freedom (df). Natural response was also estimated when control mortality occurred. If no mortality was observed in the controls then the natural response was estimated as zero.

$$\text{Synergistic Factor } (SF) = \frac{LC_{50} \text{ insecticide for population}}{LC_{50} \text{ synergised insecticide for population}}$$

Results

TABLE 1

Synergism factors of analogues of piperonyl butoxide (PBO) with imidacloprid in full dose response bioassays against *Myzus persicae* clone 5191A using a 5 h pre-treatment.

| Treatment | [a]LC$_{50}$(ppm) | [b]CL 95% | Slope ± SE | [c]df | [d]$\chi^2$ | [e]SF | Number of insects |
|---|---|---|---|---|---|---|---|
| imidacloprid | 90.4 | 51.0-185 | 0.93 ± 0.07 | 58 | 193 | — | 667 |
| +1g L$^{-1}$PBO | 6.22 | 4.04-8.70 | 1.50 ± 0.14 | 86 | 154 | 14.5 | 980 |
| +1g L$^{-1}$EN 16-5 | 12.2 | 8.80-16.4 | 1.24 ± 0.09 | 89 | 105 | 7.41 | 956 |
| +1g L$^{-1}$EN 164 | 1.25 | 0.74-1.97 | 1.23 ± 0.08 | 77 | 266 | 72.4 | 869 |
| +1g L$^{-1}$EN 126 | 0.31 | 0.21-0.43 | 1.69 ± 0.14 | 87 | 154 | 292 | 911 |
| +1g L$^{-1}$EN 163 | 2.98 | 1.90-4.51 | 0.81 ± 0.05 | 80 | 138 | 30.3 | 954 |
| +1g L$^{-1}$EN 25-10 | 4.88 | 1.20-11.0 | 1.13 ± 0.15 | 33 | 84.8 | 18.5 | 389 |
| +1g L$^{-1}$EN 129 | 28.4 | 13.6-45.8 | 1.39 ± 0.19 | 42 | 70.0 | 3.18 | 499 |
| +1g L$^{-1}$EN 16-17 | 7.11 | 5.12-9.53 | 1.13 ± 0.06 | 146 | 265 | 12.7 | 1600 |
| +1g L$^{-1}$EN 16-18 | 18.4 | 9.69-29.5 | 1.14 ± 0.11 | 79 | 156 | 4.91 | 862 |
| +1g L$^{-1}$EN 14-5 | 41.5 | 26.1-62.6 | 1.12 ± 0.13 | 42 | 42.1 | 2.17 | 506 |

[a]LC$_{50}$ = Lethal concentration to kill 50% of the population,
[b]CL = Confidence limits,
[c]df = degrees of freedom,
[d]$\chi^2$ = chi-square,
[e]SF = synergism factor (LC$_{50}$ unsynergised/LC$_{50}$ synergised).

PBO =

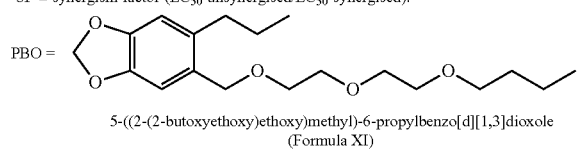

5-((2-(2-butoxyethoxy)ethoxy)methyl)-6-propylbenzo[d][1,3]dioxole
(Formula XI)

EN 16-5 =

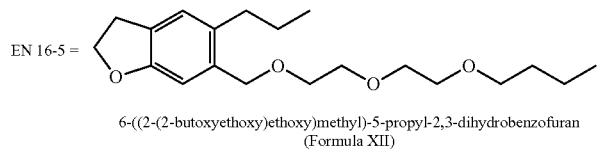 [SMILES: CCCCOCCOCCOCc1cc2c(cc1CCC)CCO2]

6-((2-(2-butoxyethoxy)ethoxy)methyl)-5-propyl-2,3-dihydrobenzofuran
(Formula XII)

EN 164 =

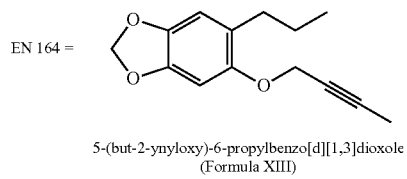 [SMILES: CC#CCOc1cc2c(cc1CCC)OCO2]

5-(but-2-ynyloxy)-6-propylbenzo[d][1,3]dioxole
(Formula XIII)

EN 126 =

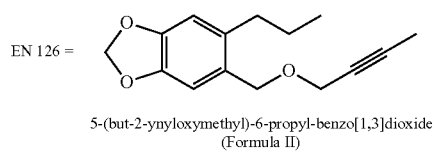 [SMILES: CC#CCOCc1cc2c(cc1CCC)OCO2]

5-(but-2-ynyloxymethyl)-6-propyl-benzo[1,3]dioxide
(Formula II)

EN 163 =

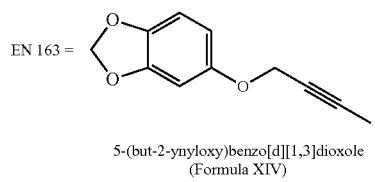

5-(but-2-ynyloxy)benzo[d][1,3]dioxole
(Formula XIV)

EN 25-10 =

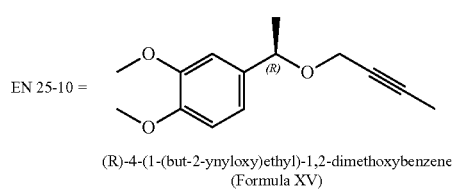

(R)-4-(1-(but-2-ynyloxy)ethyl)-1,2-dimethoxybenzene
(Formula XV)

TABLE 1-continued

Synergism factors of analogues of piperonyl butoxide (PBO) with imidacloprid in full dose response bioassays against Myzus persicae clone 5191A using a 5 h pre-treatment.

| Treatment | $^a$LC$_{50}$(ppm) | $^b$CL 95% | Slope ± SE | $^c$df | $^d\chi^2$ | $^e$SF | Number of insects |
|---|---|---|---|---|---|---|---|

EN 129 =

5-dodecylbenzo[d][1,3]dioxole
(Formula XVI)

EN 16-17 =

6-(but-2-ynyloxy)-5-propyl-2,3-dihydrobenzofuran
(Formula XVII)

EN 16-18 =

5-(but-2-ynyloxy)-2,3-dihydrobenzofuran
(Formula XVIII)

EN 14-5 =

5-((2-(2-butoxyethoxy)ethoxy)methyl)-6-propyl-2,3-dihydro-1H-indene
(Formula XIX)

CONCLUSIONS

As will be seen from the results presented above, the results obtained for EN 126 (Formula II), as represented by a synergism factor of 292, were remarkably better than those obtained for the other compounds tested and were totally unexpected.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The content of all references cited herein are incorporated herein by reference in their entirety.

The invention claimed is:

1. A composition comprising imidacloprid and the compound of Formula II,

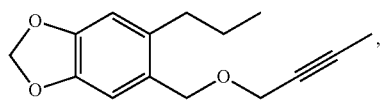

Formula II wherein the compound of Formula II is present in an amount of 1 g/L.

2. The composition according to claim 1, wherein the composition is a pesticide composition.

3. The composition according to claim 2, wherein the composition is an insecticide composition.

4. A method for controlling pests, the method comprising contacting the pests with a composition according to claim 1.

5. A method according to claim 4, wherein the pests are neonicotinoid-resistant pests or neonicotinoid-susceptible pests.

6. A method according to claim 4, wherein the pests are insects.

7. A method according to claim 4, wherein the pests are selected from sucking or chewing insects, for example from Hemiptera, Coleoptera, Diptera and Lepidoptera.

8. The composition according to claim 1, wherein the compound of Formula II is formulated in a rapid release formulation and the imidacloprid is formulated in a non-rapid release formulation.

9. The composition according to claim 8, wherein the rapid release formulation and the non-rapid release formulation are comprised in the composition in physical admixture.

* * * * *